United States Patent
Borneman et al.

(10) Patent No.: US 6,329,332 B1
(45) Date of Patent: Dec. 11, 2001

(54) PLEUROTUS PHENOL OXIDIZING ENZYMES

(75) Inventors: William S. Borneman; Elizabeth A. Bodie, both of San Carlos; Thomas P. Graycar, Pacifica; Deborah S. Winetzky, Foster City, all of CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 09/221,275

(22) Filed: Dec. 23, 1998

(51) Int. Cl.[7] .................... C11D 3/386; C11D 7/42
(52) U.S. Cl. ............... 510/320; 510/321; 510/392; 510/393
(58) Field of Search .................... 510/320, 321, 510/392, 393

(56) References Cited

FOREIGN PATENT DOCUMENTS

| | | |
|---|---|---|
| WO 96/06930 A1 | 3/1996 | (WO) . |
| WO 96/12846 A1 | 5/1996 | (WO) . |
| WO 97/08325 * | 3/1997 | (WO) . |
| WO 97/11217 A1 | 3/1997 | (WO) . |
| WO 98/27198 * | 6/1998 | (WO) . |

OTHER PUBLICATIONS

Copy of International Search Report for PCT/US99/30084, (7/01).
Giardina, P. et al., "The Gene Protein and Glycan Structures of Laccase from *Pleurotus Osteatus*," Eur. J. Biochem., vol. 235, No. 3, Feb. 1, 1996, pp. 508–515, XP–000644722.
Giardina, P. et al., "The Gene Protein and Glycan Structures of Laccase from *Pleurotus Osteatus*," EMBL Sequence Database, Apr. 20, 1995, XP–002136864.
Giardina, P. et al., "The Gene Protein and Glycan Structures of Laccase from *Pleurotus Osteatus*," EMBL Sequence Database, Jun. 30, 1994, XP–002136865.
Giardina, P. et al., "The Gene Protein and Glycan Structures of Laccase from *Pleurotus Osteatus*," EMBL Sequence Database, Nov. 1, 1997, XP–002136866.
Palmieri, G. et al., "Stability and activity of a phenol oxidase from the ligninolytic fungus *Pleurotus ostreatus*", Appl. Microbiol. Biotechnol., vol. 39, 1993, pp. 632–639, XP–000904759.

* cited by examiner

Primary Examiner—Gregory Delcotto
(74) Attorney, Agent, or Firm—Richard T. Ito (57) ABSTRACT

The present invention provides novel phenol oxidizing enzymes naturally-produced by strains of the species *Pleurotus ostreatus* which possess a pH optima in the alkaline range and which are useful in modifying the color associated with dyes and colored compounds at alkaline pH.

28 Claims, 4 Drawing Sheets

```
AGATCTACTT CCAGTTGCTT AACACCTCAT CCAGCGCGTA CTGCTACACC TACCAACGAT GTTTCCAGGC GCACGGATTC TTGCTACGCT 90
TACCTTGGCT CTTCATCTTT TACATGGGAC TCATGCTGCC ATCGGGCCCA CTGGCAACAT GTACATCGTC AACGAGGACG TCTCTCCTGA 180
TGGTTTCGCT CGTTCGTAAG TGTCTTCACT CTCAGTGTTT TGAAACCTTC AGTGCTAATT CATTATACAG GCCGGTTGTC GCTCGGTCGG 270
TGCCCGCCAC AGATCCGACG CCTGCGACAG TATCCATTCC TGGCGTTCTC GTTCAAGGAA ACAAGGTAAT TCTTGTTCTC CTCGATGGAG 360
CCGATATTTT GCTCACCCCA CGTAGGGTGA TAACTTCCAG CTGAACGTCG TCAATCAATT GTCGGACACG ACCATGTTGA AGACGACCAG 450
TATCGTACGT ACATCTGTGG TTATTTCGGA TAAACATTTA TCGTCTTTGC AGCATTGGCA CGGTTTCTTC CAAGCCGGAT CTTCGTGGGC 540
TGATGGTAGG TTCATCACTG CGCATTTACC ATACCTCGCT AACGGCGTTT TGTAGGTCCC GCTTTCGTGA CCCAATGCCC CGTCGCCTCT 630
GGGGATAGTT TCCTGTAGGT GCCACTGGCT TTATCGCCGC CCTTGATTAA TCAAAATATC CGTAGGTACA ATTTCAATGT ACCAGACCAA 720
GCTGGAACAT TTTGTAAGCC GATCATCTTG ACATCCTTTC TACATCTTCT GACCACTTCC GCAGGGTATC ACTCGCATCT TTCCACCCAA 810
TATTGTGACG GCCTCAGAGG ACCATTTGTG GTGTAAGCAA TGTCATTCCA TATGACGAAA GTGGTCTCGA CACTAACCTG CCTGCAGATA 900
CGACCCCTCG GATCCGCACT TGAGTTTATA CGATATTGAC AACGGTGAGC TCCCAACTTA TCTCGACATC AACCAACTGC ACTTTACTCA 990
CGTTCTCTCA GCTGACACGG TCATTACGCT TGAAGGATTGG GTACGCCGCC CTCTGCGAGG CCCACCGACA TCTTCTGATG TTCTCTTTAG 1080
TATCATATCG TGGCCCCTCA AAACGCGGCG ATCCCCACCC CGGATAGTAC TCTCATCAAT GGTAAAGGTC GTTACGCCGG GGGCCCTACC 1170
TCCCCTTTGT CCATCATCAA CGTCGAAAGC AACAAGCGCT ATCGTTTCAG ACTTGTCTCA TTGTCTTGCG ATCCTAATTT CACGTTCTCG 1260
ATCGACGGTC ACTCTTTGCT CGTCATTGAA GCAGATGCTG TCAACATTGT ACCCATCACC GGTTTGTCAT TTCTTTGCTG TCACTCTCGC 1350
GATGTGCTGA TCACGTATGG TCGAAATTGT AGTGGATAGT ATTCAGATCT TGCTCGGTAA GTCGTTCTCG CCTCTTCTTT GAACCCACTG 1440
CTGAGCCTCG TTTCAAGGCC AACGCTACTC CTTCGTCTTG ACTGCCGATC AGACCGTTGG CAATTACTGG ATTCGCGCGA ATCCTAACTT 1530
GGGATCGACT GGTACGGCAA TCGAAAACCA TCGTTTACGT CTTTCGCTGA TTCCTTGCCG CGCTAGGTTT CGACGGTTGT ATCAATTCCG 1620
CTATTCTTCG ATATGCTGGT GCCACTGAGG ATGACCCTAC TACAACTTCG TCGACGAGCA CCCCATTGCT GGAGACCAAC CTTGTTCCGC 1710
TTGAGAATCC TGGCGCTCCT GGCCCAGCCG TGCCTGGTGG AGCAGACATC AACATCAATC TCGCTATGGC CTTCGACTTC ACTAACTTCG 1800
AATTGACTAT CAACGGTACG CAGCATCTGA CTTGCTTTCG TTTTGATGT TTGTTTATAT CAAAGTCTAT AGGCGTTCCT TTCATTCCAC 1890
CGACTGGTGA GTGCGGCTCG AATGATGCCA GCAAAGGCAA TCACTGATGA TACTCCTGTA GCCCCTGTCC TTCTCCAAAT TCTCTCAGGA 1980
GCCTCGACTG CTGCATCGCT TCTTCCTTCC GGTAGCATTT ACGAGCTGGA AGCTAACAAA GTTGTCGAAA TCTCGATACC TGCGCTGGCT 2070
GTTGGGGGAC CCGTAAGTTT CACCCCGCTC TGCGACGGTC TATTTGCTGA CACTTCACGT GTCGGACTAG CATCCGTTCC ATCTTCACGG 2160
TGTGAGTAAT GCGGCAACTG CAACTTCTGT TTGGCTAATT GGCTTCGTAT AGCACACCTT CGACGTTATT AGGAGTGCGG GTTCCACTAC 2250
GTACAACTTC GACACTCCTG CGCGCCGCGA CGTTGTCAAC ACTGGCACTG ATGCGAACGA CAACGTCACT ATTCGCTTCG TGACCGACAA 2340
CGCAGGCCCG TGGTTCCTCC ACTGGTGAGT ATTTCGCGCA ATGTATACGG TAGGCGCATG TTGATAGTTC CCTTAGTCAT ATTGATTGGC 2430
ATCTCGAAAT GTAAGTGGCA GTCTTTACCA CCTCGTACTT GATACTAAAC GCCGTTTAGC GGTCTTGCTG TCGTTTTCGC CGAAGATGTA 2520
ACATCCATTT CGGCCCCACC TGGTATGTAT CCTTCCTGCT GCGGCTTGTG TCCCTGCTAA TTTGCATTTC TCCAGCCGCG TGGGACGACT 2610
TGTGCCCCAT CTATGACGCT TTGAGCGACA ACGACAAAGG AGGCATCGTT CCGTCCTGAT CCTCTAGA                    2678
```

FIGURE 1

```
AGAITCTACTT CCAGTTGCTT AACACCTCAT CCAGGGCGTA CTTGCTACACC TACCAACGAT GTTTCCAGGC GCACGGATTC TTGCTACGCT    90
TACCTTGGCT CTTCATCTTT TACATGGGAC TGTCTTCACT ATCGGCCCA CTGGCAACAT GTACATCGTC AACGAGACG TCTCTCCTGA   180
TGTTTTGCT CGTTGTAAG TGTCTTCACT CTCAGTGTTT TGAAAACTTC AGTGCTAATT CATTATACAG GGGGTTGTC GCTGGCTGG   270
TGCCCGCCAC AGATCCGACG CCTGGCACAG TGGCTTCTC GTTCAAGGAA ACAAGTAAT ATCGGACACG TCTGTCTC CTGATGGAG   360
CCGATATTT GCTCACCCA CGTAGGTGA TAACTTCCAG CTGAAGTG TCAATCAATT ATGGACACG ACCATGTGA AGACGACCAG   450
TATCGTAGGT ACATCGTGG TTATTTGGA TAAACATTTA TCGTCTTTGC AGCATTGGCA CGGTTTCTTC CAAGCGGAT CTTGTGGGC   540
TGATGGTAGG TTCATCACTG CGCATTTACC ATACTCGCT AACGGGTTT TGTAGGTCC GCTTTGGTGA CCCAATGCC CGTGCCTCT   630
GGGATAGTT TCCTGTAGGT GCCACTGGCT TTATGCGCC CCTTGATTAA TCAAAATATC CGTAGGTACA ATTTCAATGT AACAGACAA   720
GCTGAACAT TTTGTAAGCC GATCATCTTG ACATCCTTC TACATCTTCT GACCACTTCC GCAGGGTATC ACTGGCATCT TTCCACCCAA   810
TATTGTGACG GCCTCAGAG ACCATTGTG GTGTAAGCAA TGTCATTCCA TATGACGAAA GTGGTCTGA CACTAACTG CCTGCAGATA   900
CGACCCCTTG GATCGGCACT TGAGTTTATA CGATATTGAC AACGGTGAGC TCCCAACTTA TCTCGACATC AACCAACTGC ACTTTACTCA   990
CGTTCTCTCA GCTGACACG TCATTAGCGT TGAGGATTGG GTACCGCGC CTCTGCGAGG CCCAACGACA TCATCTGATG TTCTCTTAG  1080
TATCATATGG TGGCCCCTCA AAACGGGCG ATCCCACCC CGGATAGTAC TCTCATCAAT GGTAAAGGTC GTTACGGGG GGGCCCTACC  1170
TCCCCTTTGT CCATCATCAA CGTTGAAAGC AACAAGGGCT GGTTTCAG ACTGTTTGG TTGTCTTGCG ATCCTAATTT CAGTGTCTCG  1260
ATCGACGGTC ACTCTTTGCT CGTCATTGAA GCAAATGCTG TCAACATTGT ACCATCACC GGTTGTCAT TTCTTTGCTG TCACTCTGC  1350
GATGTGCCTGA TCAGTATGG TCGAGTATTGT AGTCGATAGT ATTCAGAATCT ATTGCTGATC AGACGTTGG GTCGTTCTG CCTCTTCTTT GAACCTACTG  1440
CTGAGCCTTG TTTCAAGGCC AACCTACTC CTTCGTCTTG ACTGCTGATCC AGACGTTGG CAATTACTGG ATTCGCCGA ATCCTAACTT  1530
GGGATCGACT GGTACGGCAA TCGAAAACTA TGGTTTACGT CTTTCGCTGA CTCCTTACCG GCTAGGTTT CGACGGTGT CGACGATTCG  1620
CTATCTTCG ATAATGCTGGT GCCACTGAGG ATGACCCTAC TGCCTGGTGG TACAACTTC AGCAGACATC AACATCAATC TGCTATGC CTGAGACTTC ATCAATTCGG  1710
TTGAGAATCC TGGCCTCCT GGCCAGTGG TGCCTGGTGG CTTGCTTCG TATGATGC TTTGGATGT CAAAGCTTAT AGGGTTCCT CTTGACTTC ACTAACTTCG  1800
AATTGACTAT CAAGGTACG CAGCATCTGA CTTGCTTCG TTTGATGT CAAAGCTTAT AGGGTTCCT TCATCCAC AGGGTTCCT  1890
CGACTGGTGA GTGGGCTCG AATGATGCCA GCAAGGCAA TCACTGATGA TACCCGTCC ACGAGCTGGA GTTGTCGAAA TCTCTCAAAT TCTCTCAGGA  1980
GCCTGGACTG CTGCATGCT TCTTCCTTCC GGTAGCATTT TGGACGCGTC ACGAGCGTTC TATTTGCTAA CACTTCAGT GTGCCACTAG TCTCGATACC TGGCCTGGCT  2070
GTTGGGGAC CCGTAAGTTT CACCCGCTC TGGACGCGTC ACGAGCGTTC TATTTGCTAA CACTTCAGT GTGCCACTAG CATCCGTTCC ATCTTCAAGG  2160
TGTGAGTAAT GGGCAACTG CAACTTCTGT CGGCCTAAT TTCGGCTAAT TTCCGCTAAT TGCCTTCTA TAGCACACCT TGAGGTTAT TAGGAGTGGG  2250
CGTACAACTT CGACACTCCT GGGCCCCGG AGTTGTCAA CACTGGCACT GATGGGAAG ACAACGTCAC TATTGCTTC GGTTGACGACA  2340
ACCGAGCCC GTGTTCCCTC CACTGGTGAG TATTTCGGGC AATGTATACG GTACGGCGAT GTTGATTGGTT CCCTTAGTCA TATTGATTGG  2430
CATCTCGAAA TGTAAGTGCC AGCTTTTACC AGCTGTACT TGATACTAAA CGCGCCCGT GTCCCTGCT ACTTGCATTT GTGTTTTCG CGGAAGAGT  2520
GACATCCATT TGGGCCCAC CTGTATGCA TCTCTCTTG CACCCGCGT GTCCCTGCTA ACTTGCATTT CTCCAGCCGC GGGGACGAC  2610
TGTGCCCCA TATATGACTG TTTGAGCGAC AAGCACAAAG GAGGCACTG TCCGTCCTGA T                                  2671
```

PLEUROTUS PHENOL OXIDIZING ENZYMES

FIELD OF THE INVENTION

The present invention relates to phenol oxidizing enzymes, in particular, phenol oxidizing enzymes obtainable from strains of Pleurotus and methods for modifying colored compounds in textile, cleaning and pulp and paper applications at alkaline pH.

BACKGROUND OF THE INVENTION

Phenol oxidizing enzymes function by catalyzing redox reactions, i.e., the transfer of electrons from an electron donor (usually a phenolic compound) to molecular oxygen (which acts as an electron acceptor) which is reduced to $H_2O$. While being capable of using a wide variety of different phenolic compounds as electron donors, phenol oxidizing enzymes are very specific for molecular oxygen as the electron acceptor.

Phenol oxidizing enzymes can be utilized for a wide variety of applications, including the detergent industry, the paper and pulp industry, the textile industry, the food industry and the wood processing industry. Most phenol oxidizing enzymes exhibit pH optima in the acidic pH range while being inactive in neutral or alkaline pHs.

Phenol oxidizing enzymes are known to be produced by a wide variety of fungi, including species of the genera Aspergillus, Neurospora, Podospora, Botytis, Pleurotus, Fomes, Phlebia, Trametes, Polyporus, Rhizoctonia and Lentinus. However, there remains a need to identify and isolate phenol oxidizing enzymes, and organisms capable of naturally-producing phenol oxidizing enzymes, which present pH optima in the alkaline range for use in pulp and paper applications and detergent washing methods.

SUMMARY OF THE INVENTION

The present invention relates to phenol oxidizing enzymes obtainable from Pleurotus ostreatus which are capable of modifying the color associated with dyes and colored compounds having different chemical structures, in particular at alkaline pH. Based on their color modifying ability, Pleurotus ostreatus phenol oxidizing enzymes of the present invention are used, for example, for pulp and paper bleaching at alkaline pH and for bleaching the color of stains on fabric at alkaline pH.

Accordingly, the present invention provides a method for modifying the color associated with a dye or colored compound in a sample comprising the step of contacting the sample with a composition comprising a purified phenol oxidizing enzyme at alkaline pH wherein, said purified phenol oxidizing enzyme is obtainable from Pleurotus ostreatus. In one aspect of the method, the pH is between about 7.5 and about 10.5 and in another aspect, the pH is between about 8 and about 10, and in another aspect, the pH is between about 8 and about 9. In another aspect of the method, said contacting takes place at a temperature between about 18° C. and up to about 50° C. and in another aspect between about 18° C. and up to about 60° C.

Figure 1:
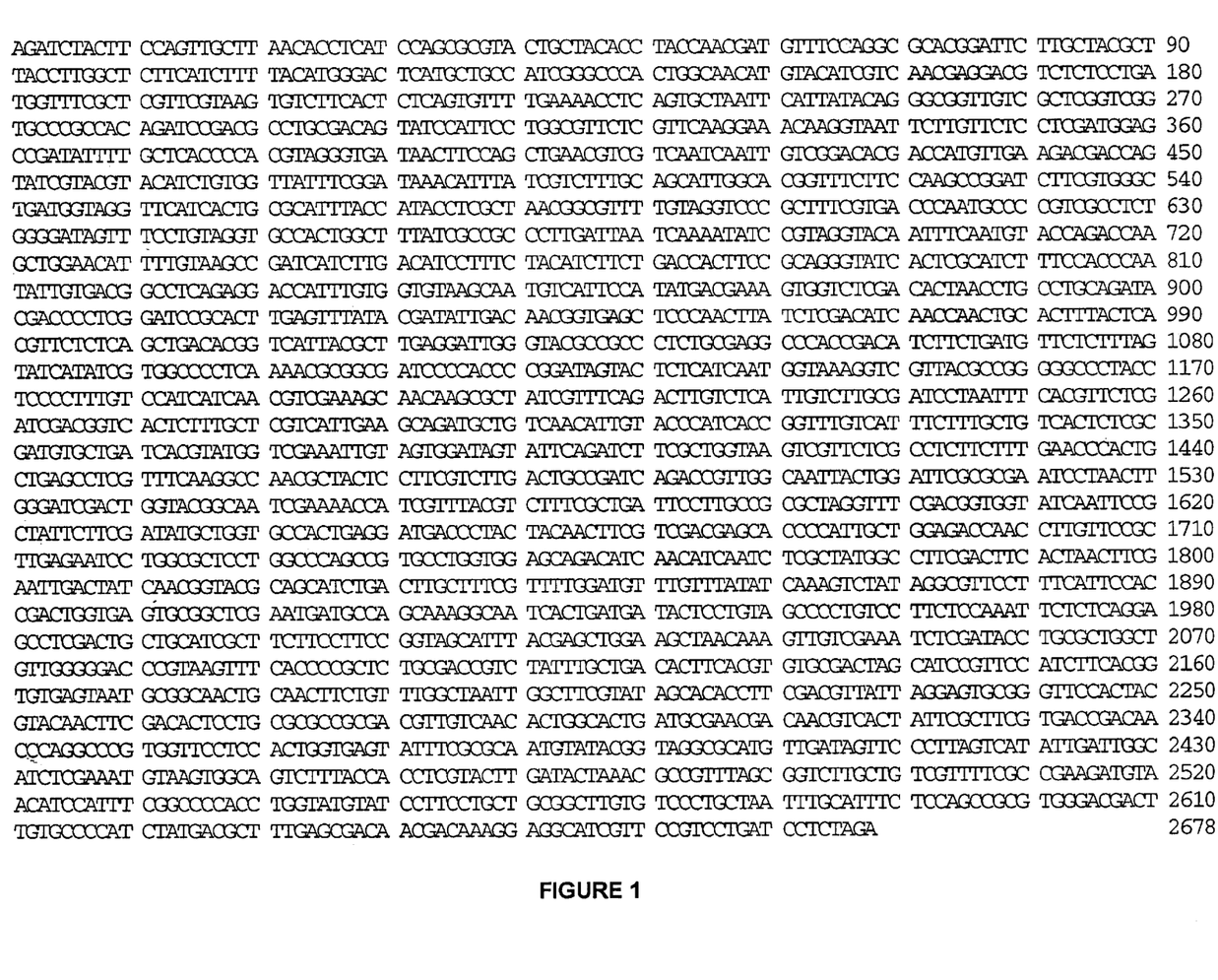
FIG. 1 illustrates the genomic nucleic acid acid sequence encoding a phenol oxidizing enzyme obtainable from Pleurotus ostreatus referred to herein as Allele A (SEQ ID NO:1).
Figure 3:
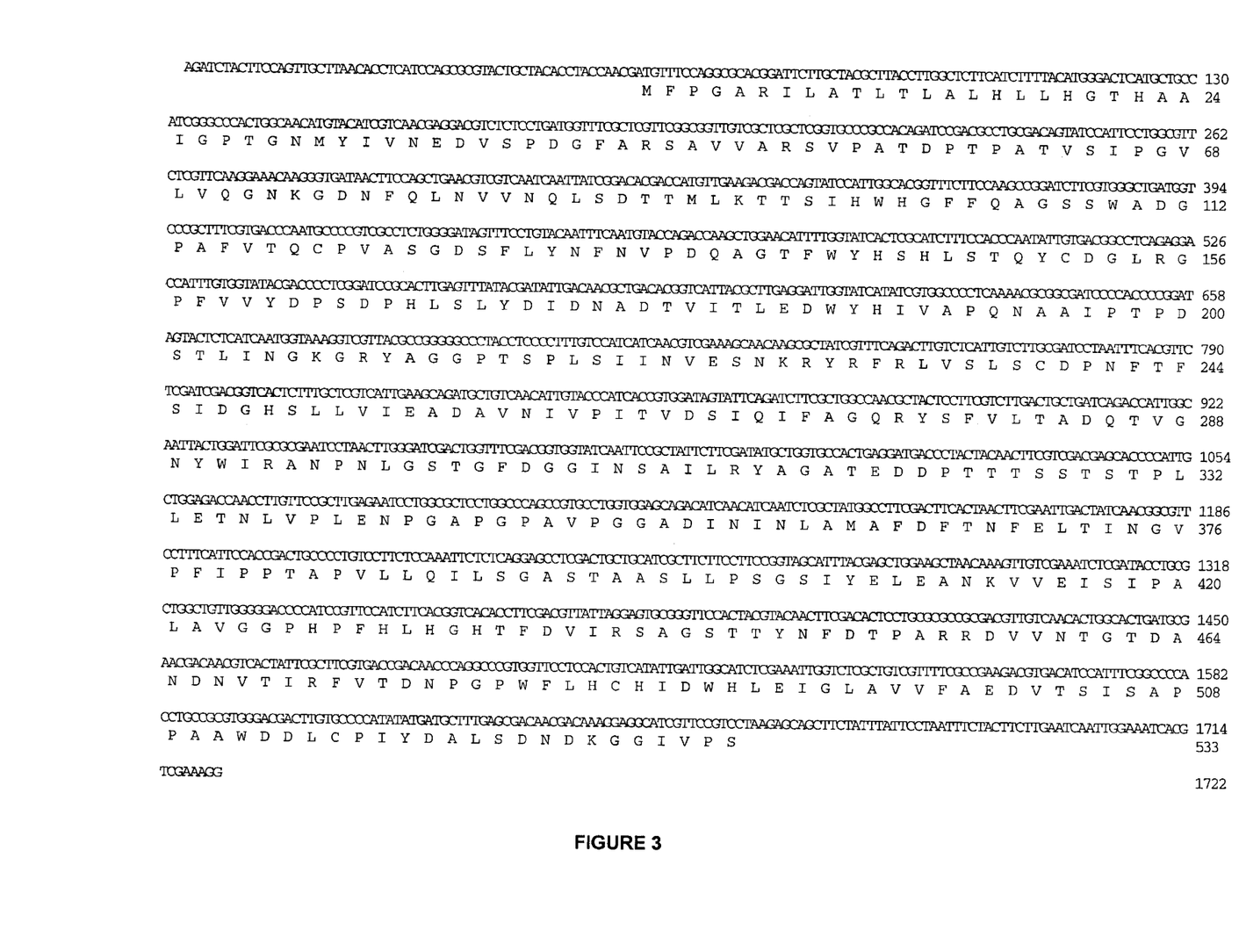
FIG. 3 illustrates the cDNA (SEQ ID NO:3) and deduced amino acid sequence (SEQ ID NO: 4) of a phenol oxidizing enzyme obtainable from Pleurotus ostreatus.

In one embodiment of the method, the phenol oxidizing enzyme is encoded by the genomic sequence as shown in FIG. 1 (SEQ ID NO:1) and in another embodiment, the phenol oxidizing enzyme is encoded by the genomic sequence as shown in FIG. 2 (SEQ ID NO: 2). In yet another embodiment of the method, the phenol oxidizing enzyme has the nucleic acid (SEQ ID NO:3) and amino acid (SEQ ID NO:4) as shown in FIG. 3. The present invention also encompasses the use of phenol oxidizing enzymes that are variations of the amino acid sequence as shown in SEQ ID NO: 4 as long as the variation is able to modify the color associated with a dye or colored compound. Accordingly, in a further embodiment, the present invention encompasses the use of a phenol oxidizing enzyme obtainable from Pleurotus ostreatus and having at least about 60%, at least 65%, at least 70%, at least 75%, at least 80%, at least 85%, at least 90% and at least 95% identity to the amino acid sequence disclosed in SEQ ID NO:4.

In one embodiment of the present invention, the phenol oxidizing enzymes are obtainable from strains of Pleurotus ostreatus, including, in particular, Pleurotus ostreatus having ATCC accession numbers 32783, 34672, 34673, 34674, 34675, 34676, 34677, 44309, 58052, 58053 and 58054. In a preferred embodiment, the phenol oxidizing enzyme is obtainable from Pleurotus ostreatus ATCC accession number 32783.

Also provided herein are detergent compositions comprising a Pleurotus ostreatus phenol oxidizing enzyme of the present invention alone or in combination with an enhancer and other detergent ingredients, including proteases, amylases and/or cellulases.

Enhancers which can be used in detergent compositions of the present invention include but are not limited to phenothiazine-10-propionic acid (PPT), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis(3-ethylbenzothiazoline-6-sulfonate) (ABTS) and 4-Hydroxy-4-biphenyl-carboxylic acid or derivatives thereof.

The present invention also encompasses expression vectors and recombinant host cells comprising nucleic acid encoding a phenol oxidizing enzyme obtainable from Pleurotus ostreatus as well as methods for purifying the phenol oxidizing enzyme from such host cells. In a preferred embodiment, the host cell is an Aspergillus species. In another embodiment, the host cell is Aspergillus niger var. awamori.

BRIEF DESCRIPTION OF THE DRAWINGS

FIG. 2 illustrates the genomic nucleic acid sequence of a phenol oxidizing enzyme obtainable from Pleurotus ostreatus referred to herein as Allele B (SEQ ID NO:2).

FIG. 4 provides an illustration of the vector pGAPT which was used for the expression of phenol oxidizing enzyme in Aspergillus. Base 1 to 1134 contains Aspergillus niger glucoamylase gene promoter. Base 1227 to 1485 and 3079 to 3100 contains Aspergillus niger glucoamylase terminator. Aspergillus nidulans pyrG gene was inserted from 1486 to 3078 as a marker for fungal transformation. The rest of the plasmid contains pUC18 sequences for propagation in E. coli. Nucleic acid encoding the Pleurotus ostreatus phenol oxidizing enzyme of SEQ ID NO:1 was cloned into the Bgl II and Xba I restriction sites.

DETAILED DESCRIPTION

Definitions

As used herein, the term phenol oxidizing enzyme refers to those enzymes which catalyze redox reactions and are specific for molecular oxygen and hydrogen peroxide as the electron acceptor.

As used herein, Pleurotus ostreatus refers to any *P. ostreatus* strain which produces a phenol oxidizing enzyme capable of modifying the color associated with dyes or colored compounds. The present invention encompasses derivatives or natural isolates of *Pleurotus ostreatus*, including progeny and mutants, as long as the derivative is able to produce a phenol oxidizing enzyme capable of modifying the color associated with dye or color compounds. In a preferred embodiment, the phenol oxidizing enzyme is obtainable from *Pleurotus ostreatus* ATCC accession number 32783. In another embodiment, the phenol oxidizing enzyme is obtainable from *Pleurotus ostreatus* having ATCC accession numbers 34672, 34673, 34674, 34675, 34676, 34677, 44309, 58052, 58053 and 58054.

As used herein in referring to phenol oxidizing enzymes, the term "obtainable from" means phenol oxidizing enzymes equivalent to those that originate from or are naturally-produced by the particular microbial strain mentioned. To exemplify, phenol oxidizing enzymes obtainable from *Pleurotus ostreatus* refer to those phenol oxidizing enzymes which are naturally-produced by *Pleurotus ostreatus*. The present invention encompasses phenol oxidizing enzymes identical to those produced by *Pleurotus ostreatus* species but which through the use of genetic engineering techniques are produced by non-Pleurotus microorganisms transformed with a gene encoding said phenol oxidizing enzyme. The present invention also encompasses mutants, variants and derivatives of the phenol oxidizing enzymes of the present invention as long as the mutant, variant or derivative phenol oxidizing enzyme is able to modify the color associated with dyes or colored compounds at an alkaline pH. In a preferred embodiment, the phenol oxidizing enzyme has the amino acid sequence as shown in SEQ ID NO:4 and is encoded by the nucleic acid sequence as shown in SEQ ID NO:3. In another embodiment of the present invention, a phenol oxidizing enzyme obtainable from *Pleurotus ostreatus* and having at least about 60% identity to SEQ ID NO: 4 is given in GenBank accession number AJ005017 wherein identity is determined by MegAlign Program from DNAstar (DNASTAR, Inc. Maidson, Wis. 53715) by Jotun Hein Method (1990, Method in Enzymology, 183: 626–645) with a gap penalty=11, a gap length penalty=3 and Pairwise Alignment Parameters Ktuple=2.

As used herein, the term 'colored compound' refers to a substance that adds color to samples, such as, textiles and pulp, or to substances which result in the visual appearance of stains.

As used herein the phrase "modify the color associated with a colored compound" or "modification of the colored compound" means that the compound is changed through oxidation such that either the color appears modified, i.e., the color visually appears to be decreased, lessened, decolored, bleached or removed, or the color is not affected but the compound is modified in such as way that it is removed from the sample. For example, in pulp and paper applications, delignification in the pulp results in higher brightness in paper made from the pulp. The present invention encompasses the modification of the color by any means including, for example, the complete removal of the colored compound from stain on a fabric by any means as well as a reduction of the color intensity or a change in the color of the compound.

As used herein, the term "mutants and variants", when referring to phenol oxidizing enzymes, refers to phenol oxidizing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phenol oxidizing enzyme. The term phenol oxidizing enzyme "derivative" as used herein refers to a portion or fragment of the full-length naturally occurring or variant phenol oxidizing enzyme amino acid sequence that retains the ability to modify the color associated with a colored compound at alkaline pH, i.e., pH between about 7.5 and about 10.5. As used herein, the term "mutants and variants", when referring to microbial strains, refers to cells that are changed from a natural isolate in some form, for example, having altered DNA nucleotide sequence of, for example, the structural gene coding for the phenol oxidizing enzyme; alterations to a natural isolate in order to enhance phenol oxidizing enzyme production; or other changes that effect phenol oxidizing enzyme expression.

The term "enhancer" or "mediator" refers to any compound that is able to modify the color associated with a dye or colored compound in association with a phenol oxidizing enzyme or a compound which increases the oxidative activity of the phenol oxidizing enzyme. The enhancing agent is typically an organic compound.

Phenol Oxidizing Enzymes and Activities

The phenol oxidizing enzymes of the present invention function by catalyzing redox reactions, i.e., the transfer of electrons from an electron donor (usually a phenolic compound) to molecular oxygen (which acts as an electron acceptor) which is reduced to water. Examples of such enzymes are laccases (EC 1.10.3.2), bilirubin oxidases (EC 1.3.3.5), phenol oxidases (EC 1.14.18.1), catechol oxidases (EC 1.10.3.1).

The phenol oxidizing enzymes of the present invention are capable of using a wide variety of different phenolic compounds as electron donors, while being very specific for molecular oxygen or hydrogen peroxide as the electron acceptor. In a preferred embodiment, the phenol oxidizing enzyme obtainable from *P. ostreatus* and having the amino acid sequence as shown in FIG. 3 is capable of modifying the color associated with dyes and colored compounds at alkaline pH.

Applications of Polyphenol Oxidizing Enzymes

Phenol oxidizing enzymes of the present invention are used in applications where it is desirable to modify the color associated with dyes or colored compounds, such as in cleaning, for removing the food stains on fabric; textiles; adhesions and coatings and paper and pulp applications. A particularly important characteristic of the *P. ostreatus* phenol oxidizing enzyme disclosed herein in FIG. 3 is that it retains activity at alkaline pHs. In particular is their high level of enzymatic activity in the pH range of from about 7.5 to about 10.5 in temperatures of up to about 60 degrees C.

Colored Compounds

In the present invention, a variety of colored compounds could be targets for oxidation by phenol oxidizing enzymes of the present invention. For example, in detergent applications, colored substances which may occur as stains on fabrics can be a target. Several types or classes of colored substances may appear as stains, such as porphyrin derived structures, such as heme in blood stain or chlorophyll in plants; tannins and polyphenols (see P. Ribéreau-Gayon, Plant Phenolics, Ed. Oliver & Boyd, Edinburgh, 1972, pp.169–198) which occur in tea stains, wine stains, banana stains, peach stains; carotenoids, the coloured substances which occur in tomato (lycopene, red), mango (carotene, orange-yellow) (G. E. Bartley et al., The Plant Cell (1995), Vol 7, 1027–1038); anthocyanins, the highly colored molecules which occur in many fruits and flowers (P. Ribéreau-Gayon, Plant Phenolics, Ed. Oliver & Boyd, Edinburgh, 1972, 135–169); and Maillard reaction products, the yellow/brown colored substances which appear upon heating of mixtures of carbohydrate molecules in the presence of protein/peptide structures, such as found in cooking oil. Pigments are disclosed in Kirk-Othmer, Encyclopedia of Chemical Technology, Third edition Vol. 17; page 788–889, a Wiley-Interscience publication. John Wiley & Sons and dyes are disclosed in Kirk-Othmer, Encyclopedia of Chemical Technology, Third edition,vol. 8, a Wiley-interscience publication. John Wiley & Sons.

Enhancers

A phenol oxidizing enzyme of the present invention can act to modify the color associated with dyes or colored compounds in the presence of an enhancer.

Enhancers are described in for example WO 95/01426 published Jan. 12, 1995; WO 96/06930, published Mar. 7, 1996; and WO 97/11217 published Mar. 27, 1997. Enhancers include but are not limited to phenothiazine-10-propionic acid (PPT), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis(3-ethylbenzothiazoline-6-sulfonate (ABTS) and 4-Hydroxy-4-biphenyl-carboxylic acid.

Purification

Phenol oxidizing enzymes of the present invention may be produced by cultivation of phenol oxidizing enzyme-producing strains, such as for example, ATCC accession number 32783 under aerobic conditions in nutrient medium containing assimiable carbon and nitrogen together with other essential nutrient(s). The medium can be composed in accordance with principles well-known in the art.

During cultivation, the phenol oxidizing enzyme-producing strains secrete phenol oxidizing enzyme extracellularly. This permits the isolation and purification (recovery) of the phenol oxidizing enzyme to be achieved by, for example, separation of cell mass from a culture broth (e.g. by filtration or centrifugation). The resulting cell-free culture broth can be used as such or, if desired, may first be concentrated (e.g. by evaporation or ultrafiltration). If desired, the phenol oxidizing enzyme can then be separated from the cell-free broth and purified to the desired degree by conventional methods, e.g. by column chromatography, or even crystallized. As described herein the second activity peak, demonstrated ABTS activity at pH 9.

The phenol oxidizing enzymes of the present invention may be isolated and purified from the culture broth into which they are extracellularly secreted by concentration of the supernatant of the host culture, followed by ammonium sulfate fractionation and gel permeation chromatography.

The phenol oxidizing enzymes of the present invention may be formulated and utilized according to their intended application. In this respect, if being used in a detergent composition, the phenol oxidizing enzyme may be formulated, directly from the fermentation broth, as a coated solid using the procedure described in U.S. Letters Pat. No. 4,689,297. Furthermore, if desired, the phenol oxidizing enzyme may be formulated in a liquid form with a suitable carrier. The phenol oxidizing enzyme may also be immobilized, if desired.

The present invention also encompasses expression vectors and recombinant host cells comprising a *Pleurotus ostreatus* phenol oxidizing enzyme of the present invention and the subsequent purification of the phenol oxidizing enzyme from the recombinant host cell.

Detergent Compositions

A phenol oxidizing enzyme of the present invention may be used in detergent or cleaning compositions. Such compositions may comprise, in addition to the phenol oxidizing enzyme, conventional detergent ingredients such as surfactants, builders and further enzymes such as, for example, proteases, amylases, lipases, cutinases, cellulases or peroxidases. Other ingredients include enhancers, stabilizing agents, bactericides, optical brighteners and perfumes. The detergent compositions may take any suitable physical form, such as a powder, an aqueous or non aqueous liquid, a paste or a gel. Examples of detergent compositions are given in WO 95/01426, published Jan. 12, 1995 and WO 96/06930 published Mar. 7, 1996.

Having thus described the phenol oxidizing enzymes of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of per cent weight per volume (w/v). As used herein, dilutions, quantities, etc., which are expressed in terms of % (v/v), refer to percentage in terms of volume per volume. Temperatures referred to herein are given in degrees centigrade (C). All references and patent publications cited herein are hereby incorporated by reference.

EXAMPLE I

This example describes the purification of the phenol oxidizing enzyme obtainable from *Pleurotus osteatus* ATCC accession number 32783.

The whole broth from a culture of ATCC accession number 32783 (produced by the process disclosed in Example III) was centrifuged for 15 minutes at 4° C. and the resulting supernatant was desalted on EconoPac 10DG columns in sodium acetate 50 mM pH 4.5 buffer. This material was filtered through a 0.45 um filter prior to loading on a Pharmacia FPLC Q-sepharose column (16/10, 48 to 60 mls load, flow rate: 2 mls/min, fraction size: 2 mls) and equilibrated in sodium acetate 50 mM pH 4.5 buffer (buffer A). Two phenol oxidizing activities were isolated from the column. The two activities were separated and eluted via sequential gradients with sodium acetate 10 mM, pH 4.5, NaCl buffer (buffer B): the first peak (peak 1) demonstrated ABTS activity at pH 5 and was eluted during the 5–30% buffer B gradient, whereas the second activity peak (peak 2), demonstrated ABTS activity at pH9 and was eluted later during the 100% buffer B step gradient.

EXAMPLE II

This example describes the genomic cloning of a phenol oxidizing enzyme activity obtained from *Pleurotus ostreatus*.

The mycelium of the *Pleurotus ostreatus* strain ATCC accession number 32783 was obtained by growing the mycelium in CSL medium for 5 days at 26° C. After physical breakage of the mycelium, genomic DNA was then extracted from mycelium using phenol/chloroform extraction. Two primers were designed based on the published pox2 gene sequence (Giardina et al., 1996, Eur. J. Biochem. 253: 508–515). The primer 1 bears following sequence: 5' AGATCTACTTCCAGTTGCTTAACACC 3' (SEQ ID NO:5). The primer 2 contains following sequence: 5' TCTA-GAGGATCAGGACGGAACGATGCCTCC 3' (SEQ ID NO:6). The Pleurotus genomic DNA was diluted was diluted 10 and 100 fold with Tris-EDTA buffer to a final concentration of 56 ng/ul and 5.6 ng/ul. Ten microliters of diluted DNA was added to the reaction mixture which contained 0.2 mM of each nucleotide (A, G. C and T), 1×reaction buffer, 0.3 microgram of primer 1 and 0.29 microgram of primer 2 in a total of a 100 microliters reaction. After heating the mixture at 100° C. for 5 minutes, 2.5 units of Taq DNA polymerase was added to the reaction mix. The PCR reaction was performed at 95° C. for 1 minute, then the primers were annealed to template at 50° C. for 1 minute and extension was done at 72° C. for 1 minute. This cycle was repeated 30 times along with an extension at 68° C. for seven minutes to achieve a gel-visible PCR fragment. The PCR fragment of about 2.6 kilobase was then cloned into plasmid vector pCR-II (Invitrogen). Both strands of the 2.6 kb insert were sequenced. Sequence data revealed that there were two alleles in the genome differing by 28 nucleotides. Allele A is shown in FIG. 1. Allele 2 is 7 nucleotides shorter at the 3' end of the gene and is shown in FIG. 2.

EXAMPLE III

Example III illustrates the cloning of the cDNA encoding a phenol oxidizing enzyme obtainable from *Pleurotus ostreatus* accession number 32738.

Pleurotus strain was grown in the following medium at pH 6.0:

| Ingredient | amount (g/l) |
| --- | --- |
| Glucose | 20 |
| Lecithin | 1.51 |
| t-aconitic acid | 1.73 |
| KH2PO4 | 3 |
| MgSO4.7H20 | 0.5 |
| CaCl2.2H20 | 0.1 |
| Ammonium tartrate | 1.2 |
| Soy peptone | 5 |
| Staley 7359 | 10 |
| benzyl alcohol | 1 |
| tween 20 | 1 |
| nitrilotriacetic acid | 0.15 |
| MnSo4.H20 | 0.05 |
| NaCl | 0.1 |
| FeSO4.7H20 | 0.01 |
| C0SO4 | 0.01 |
| CaCl2.2H20 | 0.01 |
| ZnSO4.7h20 | 0.01 |
| CuSO4 | 0.001 |
| ALK(SO4)2.12H2) | 0.001 |
| H3BO3 | 0.001 |
| NaMoO4.2H20 | 0.001 | at 26° C. for 7 days and induced with 0.8 uM Xylidine for additional 3 days. After physical breakage of the mycelium, RNA was then extracted from mycelium using phenol/chloroform extraction. The total cDNA was synthesized by reverse transcriptase using 1.6 micrograms of RNA in 20 microliter reaction containing 0.34 micrograms oligo $dT_{18}$ primer, 0.5 mM of each of four nucleotides (A, G, C and T), 20 units of RNA inhibitor and 200 units of reverse transcriptase. The cDNA was then cloned by PCR using the following two primers: AGATCTACTTCCAGTTGCT-TAACC (primer 3; SEQ ID NO:7) and CCTTTCGACGT-GATTTCC (primer 4; SEQ ID NO.8). The PCR fragment was sequenced to confirm identity. The cDNA sequence of 1722 bp is shown in FIG. 3.

Comparison of the cDNA with genomic DNA revealed that there were 19 introns in the genomic DNA. The protein translation start site (ATG) is at nucleotide #59 to #61 and the translation stop site is at nucleotide #1658 to #1660. Putative protein sequence translated from cDNA contains 533 amino acids. The deduced protein sequence is shown in FIG. 3.

EXAMPLE IV

This Example illustrates the expression of the phenol oxidase gene obtainable from *Pleurotus ostreatus* in *Aspergillus niger* var. *awamori*

Figure 4:
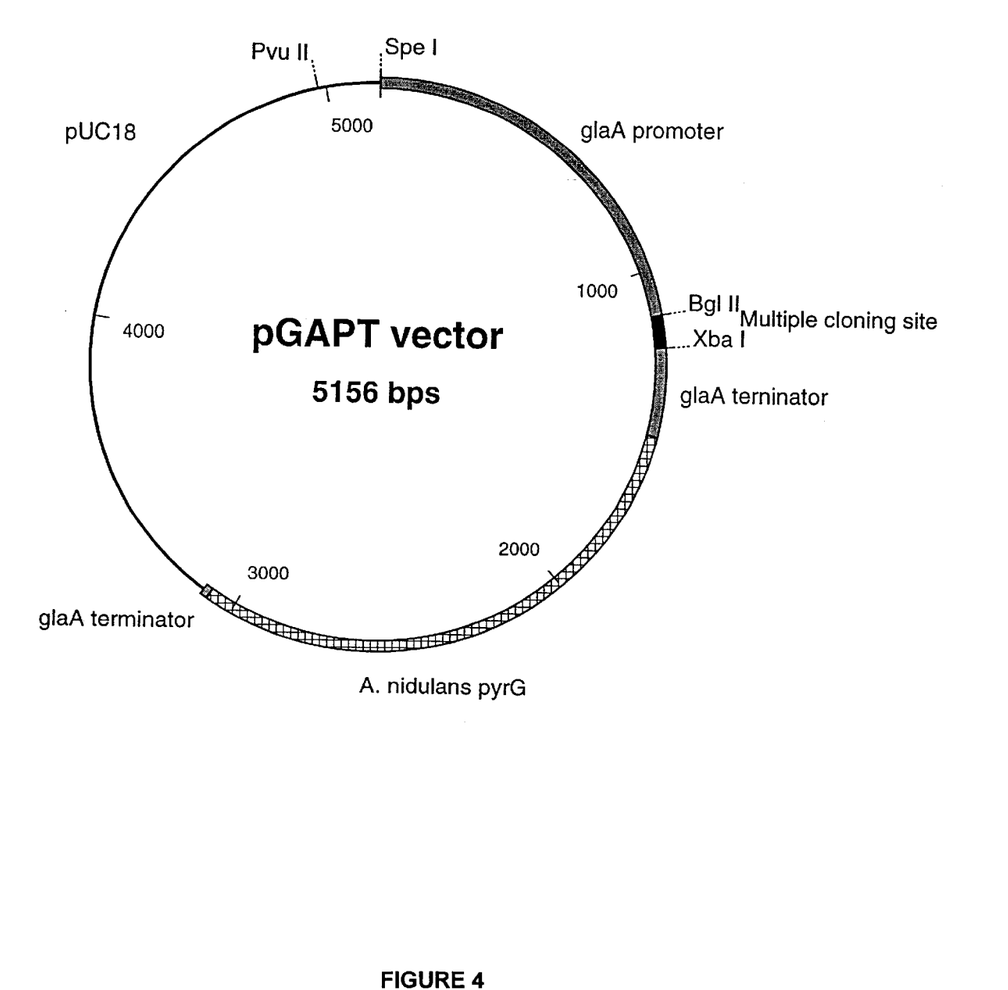

The vector pGAPT as shown in FIG. 4 was used for expressing the phenol oxidase gene contains the *Aspergillus niger* glucoamylase gene promoter (from bases 1 to 1134) and terminator (from bases 1227 to 1485), a multicloning site (from bases 1135 to 1227), *Aspergillus nidulans* pyrG gene (from bases 1486 to 3078) as selection marker for fungal transformation and puc18 plasmid backbone for propagation in *E. coli*. The Bgl II to Spe I fragment containing *Pleurotus ostreatus* phenol oxidase gene was cloned into the Bgl II to Xba I site of vector pGAPT to create an expression plasmid. The plasmid was then transformed into *Aspergillus niger* var. *awamori* strain (dgr246:p2, Appl. Micro. Biotechnol, 1993, 39:738–743) by standard PEG methods. Transformants were selected on plates without uridine. Seventeen transformants were grown on CMA plates and then transferred to the shake flasks containing CSL medium and grew for 3 days. 5 ml of the CSL cultures were then transferred to the Clofine medium and grew for 8 days at 30° C. CMA plates contain: glucose, 20 g/l; Malt extract, 20 g/L; Bacto Peptone, 1 g/L and Bacto agar, 20 g/L). CSL medium is described in Dunn-Coleman et al., 1991, Bio/Technology 9:976–981. CSL special medium is CSL medium with the glucose and fructose eliminated. ABTS assays indicated that the best transformants produced about 0.9 unit/ml of recombinant phenol oxidizing activity. Three best transformants were spore purified and ABTS activity was assayed for 8 day-old Clofine culture. Spore purified strain produced about the same units of recombinant Pleurotus phenol oxidase in *Aspergillus niger* var. *awamori* (0.88 units/ml).

EXAMPLE V

The following example describes the ABTS assay used for the determination of phenol oxidizing activity. The ABTS assay is a spectrophotometric activity assay which uses the following reagents: assay buffer=50 sodium acetate, pH 5.0; 50 mM sodium phosphate, pH 7.0; 50 mM sodium carbonate, pH 9.0. The ABTS (2,2'-azinobis 3 ethylbenzothiazoline-6-sulphonic acid]) is a 4.5 mM solution in distilled water.

0.75 ml assay buffer and 0.1 ml ABTS substrate solution are combined, mixed and added to a cuvette. A cuvette containing buffer-ABTS solution is used as a blank control. 0.05 ml of enzyme sample is added, rapidly mixed and placed into the cuvette containing buffer-ABTS solution. The rate of change in absorbance at 420 nm is measure, $\Delta$OD 420/minute, for 15 seconds (or longer for samples having activity rates <0.1) at 30° C. Enzyme samples having a high rate of activity are diluted with assay buffer to a level between 0.1 and 1.

As disclosed in Example 1, there were two enzyme peaks both of which were active on ABTS substrate at pH 5, however, only the protein which eluted last off of the Q-Sepharose purification column had activity at pH 9 in the above ABTS assay.

EXAMPLE VI

The following example describes the shake flask pulp bleaching protocol used to determine the activity of the *Pleurotus ostreatus* phenol oxidizing enzyme.

The buffer used was 50 mM Na Acetate, pH 5 or 50 mM Tris pH 8.5. Softwood, oxygen delignified pulp was used with a of kappa 17.3. The enzyme was *Pleurotus ostreatus* supernatent obtained as described above and was dosed at 10 ABTS units per g of pulp. The mediator was 1-nitroso-2-napthol-3,6-disulfonic acid, disodium hydrate (Sigma).

250 ml of pre-warmed buffer was placed in a graduated cylinder. 10 g of wet pulp (at 72% moisture=2.8 g dry pulp) was placed into a standard kitchen blender with ~120 ml buffer. The pulp was blended on the highest setting for about 30 seconds. The resulting slurry was placed into a 2.8 L large-mouth shake flask (residual pulp is rinsed out of the blender with remaining buffer and spatula). This results in about a 1% consistency in the flask (2.8 g/250 ml).

The enzyme and mediator were added to the above. A control was also done without enzyme. The opening of the flask was covered with 2 thickness cheese cloth and secured with rubber band. The flasks were placed into a shaker and incubated for 2 hours at ~55° C. and 350 rpm.

At the end of the incubation time, 500 mls of 2% NaOH was added directly into the flasks and the shaker temperature was set to 70° C. and allowed to incubate for 1.5 hours at 250 rpm. The temperature in the shaker reached around 65–70° C. by the end of this time. The flask contents were filtered through buchner funnels. The pulp slurries were poured directly into the funnels, without vacuum and were allowed to slowly drip which set up a filter layer inside the funnel.

Once most of the flask contents were in the funnel, a light vacuum was applied to pull the material into a cake inside the funnel. The filtrate (liquid) was poured back into the original shake flask and swirled to wash residual pulp from the sides. The filtrate was poured back on top of the filter cake. The end result was a fairly clear light golden colored filtrate with most of the pulp caught in the funnel. The filter cake was washed without vacuum, by gently pouring 1 liter of DI water over the filter cake and letting it drip through on its own. A vacuum was applied only at the end to suck the cake dry. The filter cakes were dryed in the funnels overnight in a 100° C. oven. The dried pulp was manually scraped from the cooled funnels the next day. Microkappa determinations based on the method of the Scandinavian Pulp, Paper and Board Testing committee Scan-c 1:77 (The Scandinavian Pulp Paper and Board Testing committee Box 5604,S-114, 86 Stockholm, Sweden), were performed to determine % delignification.

|  | Kappa no. |
|---|---|
| Orginal Pulp | 17.28 |
| Washed pulp | 15.51 |
| Control (50 mM Tris pH 8.5) | 14.02 |
| *P. ostreatus* (50 mM tris, pH 8.5) | 13.5 |

EXAMPLE VII

Example I illustrates the dose efficiency curve (DEC), temperature profile, and pH curve for *Pleurotus ostreatus* phenol oxidizing enzyme as shown in SEQ ID NO:4.

Methods and Materials

| | |
|---|---|
| CIE: | Commission International de l'Eclairage, 1931 |
| D65/10°: | D65 is the illuminate; 10° refers to a 1964 10° Standard Observer |
| DL*: | Lightness factor |
| Equipment: | Terg-O-Tometer |
| Temperature: | 40° C. |
| RPM's: | 100 |
| Volume: | 1 liter/terg. pot |
| Buffer/Water hardness: | 120 mM Tris pH 8.0, 150 ppm CaCO$_3$ |
| Run time: | 3 hours |
| Enzyme dosage: | SEQ ID NO:4, 150 U/L (ABTS assay, pH 5.5) |
| Swatches: | BC-1, Tea for high temperature on cotton, (2/pot) |
| | BC-2, Coffee on cotton, (2/pot) |
| Rinse: | Cold water in US washing machine |
| Wash Conditions Evaluated: | Buffer Alone (without enzyme or mediator) |
| | Buffer + enzyme |
| | Buffer + Mediator |
| | Buffer + enzyme + Mediator |
| Evaluation Method: | Reflectometer used to evaluate the L* value prior and post cleaning cycle. |

Testing was done in a Terg-O-Tometer to determine which mediators would give a bleaching effect on coffee and tea swatches with phenol oxidizing enzyme as shown in SEQ ID NO:4. Mediator, enzyme and swatches were added to the appropriate terg. pots (after the buffer with water hardness was placed in each Terg-O-Tometer pot) and allowed to warm to 40° C. After testing was completed the swatches were evaluated by comparing the DL* value for each condition. L* values reported are an average of 6 readings, 3 per swatch and are based on the CIELAB. Results are presented in Table 1 and show performance benefits when using SEQ ID NO:4 enzyme with 1-Nitroso-2-Naphthol-3, 6Disulfonic Acid, (NNDA) at 1 mM, 2,2'Azino-bis(3-Ethylbenz-thiazoline-6-sulfonic acid), (ABTS) 1 mM, and 4'-Hydroxy-4-biphenyl-carboxylic acid, (HPC) 1 mM.

TABLE 1

| L*Values Condition | Tea ΔL* | Coffee ΔL* |
|---|---|---|
| Buffer | 0.02 | 0.15 |
| Buffer + enzyme | −0.20 | 0.46 |
| Buffer + NNDA | 0.54 | 0.83 |
| Buffer + NNDA + enzyme | 4.78 | 5.11 |
| Buffer + ABTS | −0.91 | −0.56 |
| Buffer + ABTS + enzyme | 1.25 | 2.81 |
| Buffer + 4-Hydroxy | −1.70 | −1.26 |
| Buffer + 4-Hydroxy + enzyme | 1.73 | 2.09 |

Table 1 Results indicate that the most significant results were with the NNDA mediator.

EXAMPLE VIII

Example VII illustrates an enzyme dose response curve.

| Experimental Conditions and Materials | |
|---|---|
| Equipment: | 12 well Cell Well plate Shaker |
| Temperature: | 40° C. |
| RPM's: | ~100 |
| Volume: | 4 mLs/well |
| Buffer: | 50 mM Tris, pH 8.0 |
| Run time: | 3 hours |
| Enzyme: | SEQ ID NO:4 *Pleurtus ostreafus* |
| Mediator Tested/Concentration: | 1-Nitroso-2-Naphthol-3,6Disulfonic Acid, (NNDA)/1 mM |
| Swatches Evaluated: | BC-2, Coffee on cotton, (1/well) BC-3, Tea on cotton, (1/well) |
| Rinse Method: | $dH_2O$ in strainer |
| Wash Conditions Evaluated: | Buffer Alone (without enzyme or mediator) Buffer + Enzyme Buffer + Mediator Buffer + Enzyme + Mediator |
| Evaluation Method: | Reflectometer used to evaluate the L* value prior and post cleaning cycle. |

A dose response curve for enzyme having SEQ ID NO:4 was determined using the NNDA mediator. Testing was performed in Cell Well plates (12 well/plate) with test volumes of 4 mL/well (50 mM Tris pH8). Enzyme dosage varied from 0 to 0.2 ABTS U/mL with a constant dosage of mediator. Each test condition was run in duplicate wells. Results are reported as the difference between the post wash and pre-wash L* values. DL* on coffee for each condition can be seen in Table 2. DL* on tea for each condition can be seen in Table 3.

TABLE 2

Coffee on Cotton

| Enzyme Dose (ABTS U/mL) | with Mediator ΔL* | without Mediator ΔL* |
|---|---|---|
| 0 | 0.76 | 0.76 |
| 0.02 | 2.01 | 0.78 |
| 0.06 | 3.30 | 1.21 |
| 0.09 | 3.73 | 0.44 |
| 0.12 | 4.08 | 0.65 |
| 0.2 | 4.27 | 1.48 |

Result from Table 2, indicate that increased bleaching is observed as enzyme dose increases.

TABLE 3

Tea on Cotton

| Enzyme Dose (ABTS U/mL) | with Mediator ΔL* | without Mediator ΔL* |
|---|---|---|
| 0 | 0.94 | 0.94 |
| 0.02 | 1.11 | 0.85 |
| 0.06 | 1.90 | 0.45 |
| 0.09 | 3.01 | 0.96 |
| 0.12 | 2.18 | 0.42 |
| 0.2 | 2.72 | 0.84 |

Results from Table 3 indicate that the mediator is needed for bleaching effect when using enzyme having SEQ ID NO:4. Additionally, increased bleaching is observed as the enzyme dose increases.

EXAMPLE IX

Temperature profiles for enzyme and mediator NNDA were determined by the same method as in Example VII. In this case, enzyme dosage was held constant at 112 ABTS U/mL and the temperature was varied from one plate to another. Temperatures tested were 20, 40, and 60° C. Results are documented in Table 4 and Table 5.

TABLE 4

Coffee on Cotton

| Condition | 20° C. ΔL* | 40° C. ΔL* | 60° C. ΔL* |
|---|---|---|---|
| Buffer | 0.42 | 1.10 | 0.97 |
| enzyme | 0.75 | 0.79 | 1.43 |
| NNDA | 0.66 | 0.98 | 1.15 |
| enzyme + NNDA | 1.31 | 4.16 | 5.59 |

TABLE 5

Tea on Cotton

| Condition | 20° C. ΔL* | 40° C. ΔL* | 60° C. ΔL* |
|---|---|---|---|
| Buffer | 0.72 | 0.642 | 0.78 |
| enzyme | 0.64 | 0.205 | 0.757 |
| NNDA | 0.3 | 0.887 | 0.637 |
| enzyme + NNDA | 0.725 | 2.497 | 4.435 |

EXAMPLE X pH profiles for SEQ ID NO:4 enzyme and NNDA were determined by same method as in Example VIII In this experiment enzyme dosage was held constant at 112 ABTS U/mL and the pH was varied using either 50 mM Acetic or 50 mM Tris buffer. pH's tested were tested at 7.95, 8.3, and 8.7. Results are documented in Table 6.

TABLE 6

| Laccase + NNDA | pH 7.95 ΔL* | pH 8.3 ΔL* | pH 8.7 ΔL* |
|---|---|---|---|
| Coffee on Cotton | 5.35 | 4.74 | 5.32 |
| Tea on Cotton | 6.39 | 6.08 | 4.52 |

Controls for pH 7.95 data were at pH 8.16:
Buffer only: 2.18
Enzyme: 3.3
Controls for pH 8.3 data were at 8.55:
Buffer only: 1.99
Enzyme: 2.58
Controls for pH 8.7 data were at 8.88:
Buffer only: 2.82
Enzyme: 2.99

We claim:

1. A method for modifying the color associated with a dye or colored compound in a sample comprising, contacting the sample with a composition comprising a purified phenol oxidizing enzyme at alkaline pH, wherein said purified phenol oxidizing enzyme has at least 70% identity to SEQ ID NO:4, and is obtainable from *Pleurotus ostreatus*.

2. The method according to claim 1 wherein the *Pleurotus ostreatus* is selected from the group consisting of *Pleurotus ostreatus* ATCC accession number 32783, 34672, 34673, 34674, 34675, 34676, 34677, 44309, 58052, 58053 and 58054.

3. The method of claim 1 wherein said phenol oxidizing enzyme has the amino acid sequence as shown in SEQ ID NO: 4, or a variation thereof capable of modifying the color associated with a dye or colored compound.

4. A method for modifying the color associated with a dye or colored compound in a sample comprising, contacting the sample with a composition comprising a purified phenol oxidizing enzyme at alkaline pH, wherein said purified phenol oxidizing enzyme is obtained from *Pleurotus ostreatus*, wherein said phenol oxidizing enzyme is encoded by the nucleic acid sequence as shown in SEQ ID NO: 1, SEQ ID NO:2 or SEQ ID NO:3.

5. The method of claim 1 wherein the composition further comprises an enhancer.

6. The method of claim 1 wherein the pH is between about 7.5 and about 10.5.

7. The method of claim 1 wherein the pH is between about 8 and about 10.

8. The method of claim 1 wherein the pH is between about 8 and about 9.

9. The method of claim 1 wherein said contacting takes place at a temperature between about 18° C. and about 60° C.

10. The method of claim 5 wherein the enhancer is selected from the group consisting of phenothiazine-10-propionic acid (PPT), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis(3-ethylbenzothiazoline-6-sulfonate (ABTS) and 4-Hydroxy-4-biphenyl-carboxylic acid or derivatives thereof.

11. The method of claim 1 wherein the colored compound is selected from the group consisting of tannins, carotenoids, and anthocyanins.

12. The method of claim 3 wherein said variation has at least about 80% identity to SEQ ID NO:4.

13. A detergent composition comprising a phenol oxidizing enzyme obtainable from *Plerotus ostreatus* wherein said enzyme has at least about 70% identity to SEQ ID NO: 4 and is capable of modifying the color associated with a colored compound at alkaline pH.

14. The detergent composition of claim 13 wherein said phenol oxidizing enzyme has the amino acid sequence as shown in SEQ ID NO:4, or a variation thereof capable of modifying the color associated with a dye or colored compound.

15. The method of claim 14 wherein said variation has at least about 80% identity to SEQ ID NO:4.

16. The detergent composition of claim 13 further comprising an enhancer.

17. The detergent composition of claim 16 wherein the enhancer is selected from the group consisting of phenothiazine-10-propionic acid (PPT), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'- azino-bis(3-ethylbenzothiazoline-6-sulfonate (ABTS) and 4-Hydroxy-4-biphenyl-carboxylic acid or derivatives thereof.

18. The method of claim 14 wherein said variation has at least about 80% identity to SEQ ID NO:4.

19. The method of claim 14 wherein said variation has at least about 95% identity to SEQ ID NO:4.

20. The method of claim 4 wherein the composition further comprises an enhancer.

21. The method of claim 4 wherein the pH is between about 7.5 and about 10.5.

22. The method of claim 4 wherein the pH is between about 8 and about 10.

23. The method of claim 4 wherein the pH is between about 8 and about 9.

24. The method of claim 4 wherein said contacting takes place at a temperature between about 18° C. and about 60° C.

25. The method of claim 19 wherein the enhancer is selected from the group consisting of phenothiazine-10-propionic acid (PPT), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis(3-ethylbenzothiazoline-6-sulfonate (ABTS) and 4-Hydroxy-4-biphenyl-carboxylic acid or derivatives thereof.

26. The method of claim 4 wherein the colored compound is selected from the group consisting of tannins, carotenoids, and anthocyanins.

27. The method of claim 4 wherein said variation has at least about 80% identity to SEQ ID NO:4.

28. The method of claim 4 wherein said variation has at least about 95% identity to SEQ ID NO:4.

\* \* \* \* \*

SEQUENCE LISTING

<160> NUMBER OF SEQ ID NOS: 8

<210> SEQ ID NO 1
<211> LENGTH: 2678
<212> TYPE: DNA
<213> ORGANISM: Pleurotus ostreatus

<400> SEQUENCE: 1

```
agatctactt ccagttgctt aacacctcat ccagcgcgta ctgctacacc taccaacgat      60
gtttccaggc gcacggattc ttgctacgct taccttggct cttcatcttt tacatgggac     120
tcatgctgcc atcgggccca ctggcaacat gtacatcgtc aacgaggacg tctctcctga     180
tggtttcgct cgttcgtaag tgtcttcact ctcagtgttt tgaaaacctc agtgctaatt     240
cattatacag ggcggttgtc gctcggtcgg tgcccgccac agatccgacg cctgcgacag     300
tatccattcc tggcgttctc gttcaaggaa acaaggtaat tcttgttctc ctcgatggag     360
ccgatatttt gctcacccca cgtagggtga taacttccag ctgaacgtcg tcaatcaatt     420
gtcggacacg accatgttga agacgaccag tatcgtacgt acatctgtgg ttatttcgga     480
taaacattta tcgtctttgc agcattggca cggtttcttc caagccggat cttcgtgggc     540
tgatggtagg ttcatcactg cgcatttacc ataccctcgt aacggcgttt tgtaggtccc     600
gctttcgtga cccaatgccc cgtcgcctct ggggatagtt tcctgtaggt gccactggct     660
ttatcgccgc ccttgattaa tcaaaatatc cgtaggtaca atttcaatgt accagaccaa     720
gctggaacat tttgtaagcc gatcatcttg acatcctttc tacatcttct gaccacttcc     780
gcagggtatc actcgcatct ttccacccaa tattgtgacg gcctcagagg accatttgtg     840
gtgtaagcaa tgtcattcca tatgacgaaa gtggtctcga cactaacctg cctgcagata     900
cgacccctcg gatccgcact tgagtttata cgatattgac aacggtgagc tcccaactta     960
tctcgacatc aaccaactgc actttactca cgttctctca gctgacacgg tcattacgct    1020
tgaggattgg gtacgccgcc ctctgcgagg cccaccgaca tcttctgatg ttctcttttag    1080
tatcatatcg tggcccctca aaacgcggcg atccccaccc cggatagtac tctcatcaat    1140
ggtaaaggtc gttacgccgg gggccctacc tccccttttgt ccatcatcaa cgtcgaaagc    1200
aacaagcgct atcgtttcag acttgtctca ttgtcttgcg atcctaattt cacgttctcg    1260
atcgacggtc actcttttgct cgtcattgaa gcagatgctg tcaacattgt acccatcacc    1320
ggtttgtcat ttctttgctg tcactctcgc gatgtgctga tcacgtatgg tcgaaattgt    1380
agtggatagt attcagatct tcgctggtaa gtcgttctcg cctcttcttt gaacccactg    1440
ctgagcctcg tttcaaggcc aacgctactc cttcgtcttg actgccgatc agaccgttgg    1500
caattactgg attcgcgcga atcctaactt gggatcgact ggtacggcaa tcgaaaacca    1560
tcgtttacgt ctttcgctga ttccttgccg cgctaggttt cgacggtggt atcaattccg    1620
ctattcttcg atatgctggt gccactgagg atgaccctac tacaacttcg tcgacgagca    1680
ccccattgct ggagaccaac cttgttccgc ttgagaatcc tggcgctcct ggcccagccg    1740
tgcctggtgg agcagacatc aacatcaatc tcgctatggc cttcgacttc actaacttcg    1800
aattgactat caacggtacg cagcatctga cttgctttcg ttttggatgt tgtttatat    1860
caaagtctat aggcgttcct ttcattccac cgactggtga gtgcggctcg aatgatgcca    1920
gcaaaggcaa tcactgatga tactcctgta gcccctgtcc ttctccaaat tctctcagga    1980
gcctcgactg ctgcatcgct tcttccttcc ggtagcattt acgagctgga agctaacaaa    2040
```

```
gttgtcgaaa tctcgatacc tgcgctggct gttgggggac ccgtaagttt cacccccgctc   2100 tgcgaccgtc tatttgctga cacttcacgt gtgcgactag catccgttcc atcttcacgg   2160
tgtgagtaat gcggcaactg caacttctgt ttggctaatt ggcttcgtat agcacacctt   2220
cgacgttatt aggagtgcgg gttccactac gtacaacttc gacactcctg cgcgccgcga   2280
cgttgtcaac actggcactg atgcgaacga caacgtcact attcgcttcg tgaccgacaa   2340
cccaggcccg tggttcctcc actggtgagt atttcgcgca atgtatacgg taggcgcatg   2400
ttgatagttc ccttagtcat attgattggc atctcgaaat gtaagtggca gtctttacca   2460
cctcgtactt gatactaaac gccgtttagc ggtcttgctg tcgttttcgc cgaagatgta   2520
acatccattt cggccccacc tggtatgtat ccttcctgct gcggcttgtg tccctgctaa   2580
tttgcatttc tccagccgcg tgggacgact tgtgccccat ctatgacgct ttgagcgaca   2640
acgacaaagg aggcatcgtt ccgtcctgat cctctaga                           2678

<210> SEQ ID NO 2
<211> LENGTH: 2671
<212> TYPE: DNA
<213> ORGANISM: Pleurotus ostreatus

<400> SEQUENCE: 2
agatctactt ccagttgctt aacacctcat ccagcgcgta ctgctacacc taccaacgat   60
gtttccaggc gcacggattc ttgctacgct taccttggct cttcatcttt tacatgggac   120
tcatgctgcc atcgggccca ctggcaacat gtacatcgtc aacgaggacg tctctcctga   180
tggtttcgct cgttcgtaag tgtcttcact ctcagtgttt tgaaaacctc agtgctaatt   240
cattatacag ggcggttgtc gctcgctcgg tgcccgccac agatccgacg cctgcgacag   300
tatccattcc tggcgttctc gttcaaggaa acaaggtaat tcttgttctc ctcgatggag   360
ccgatatttt gctcacccca cgtagggtga taacttccag ctgaacgtcg tcaatcaatt   420
atcggacacg accatgttga agacgaccag tatcgtacgt acatctgtgg ttatttcgga   480
taaacattta tcgtctttgc agcattggca cggtttcttc caagccggat cttcgtgggc   540
tgatggtagg ttcatcactg cgcatttacc ataccctgct aacggcgttt tgtaggtccc   600
gctttcgtga cccaatgccc cgtcgcctct ggggatagtt tcctgtaggt gccactggct   660
ttatcgccgc ccttgattaa tcaaaatatc cgtaggtaca atttcaatgt accagaccaa   720
gctggaacat tttgtaagcc gatcatcttg acatcctttc tacatcttct gaccacttcc   780
gcagggtatc actcgcatct ttccacccaa tattgtgacg gcctcagagg accatttgtg   840
gtgtaagcaa tgtcattcca tatgacgaaa gtggtctgga cactaacctg cctgcagata   900
cgacccctcg gatccgcact tgagtttata cgatattgac aacggtgagc tcccaactta   960
tctcgacatc aaccaactgc actttactca cgttctctca gctgacacgg tcattacgct   1020
tgaggattgg gtacgccgcc ctctgcgagg cccaccgaca tcatctgatg ttctctttag   1080
tatcatatcg tggccccctca aaacgcggcg atccccaccc cggatagtac tctcatcaat   1140
ggtaaaggtc gttacgccgg gggccctacc tccccttgt ccatcatcaa cgtcgaaagc   1200
aacaagcgct atcgtttcag acttgtctca ttgtcttgcg atcctaattt cacgttctcg   1260
atcgacggtc actctttgct cgtcattgaa gcagatgctg tcaacattgt acccatcacc   1320
ggtttgtcat ttcttgctg tcactctcgc gatgtgctga tcacgtatgg tcgaaattgt   1380
agtggatagt attcagatct tcgctggtaa gtcgttctcg cctcttcttt gaacctactg   1440
```

-continued

```
ctgagcctcg tttcaaggcc aacgctactc cttcgtcttg actgctgatc agaccgttgg       1500
caattactgg attcgcgcga atcctaactt gggatcgact ggtacggcaa tcgaaaacta       1560
tcgtttacgt ctttcgctga ctccttaccg ggctaggttt cgacggtggt atcaattccg       1620
ctattcttcg atatgctggt gccactgagg atgaccctac tacaacttcg tcgacgagca       1680
ccccattgct ggagaccaac cttgttccgc ttgagaatcc tggcgctcct ggcccagccg       1740
tgcctggtgg agcagacatc aacatcaatc tcgctatggc cttcgacttc actaacttcg       1800
aattgactat caacggtacg cagcatctga cttgctttcg ttttggatgt ttgtttatat       1860
caaagtctat aggcgttcct ttcattccac cgactggtga gtgcggctcg aatgatgcca       1920
gcaaaggcaa tcactgatga tactcctgta gcccctgtcc ttctccaaat tctctcagga       1980
gcctcgactg ctgcatcgct tcttccttcc ggtagcattt acgagctgga agctaacaaa       2040
gttgtcgaaa tctcgatacc tgcgctggct gttgggggac ccgtaagttt cacccccgctc      2100 tgcgaccgtc tatttgctaa cacttcacgt gtgcgactag catccgttcc atcttcacgg       2160
tgtgagtaat gcggcaactg caacttctgt ttcggctaat tggcttcgta tagcacacct       2220
tcgacgttat taggagtgcg ggttccacta cgtacaactt cgacactcct gcgcgccgcg       2280
acgttgtcaa cactggcact gatgcgaacg acaacgtcac tattcgcttc gtgaccgaca       2340
acccaggccc gtggttcctc cactggtgag tatttcgcgc aatgtatacg gtaggcgcat       2400
gttgatggtt cccttagtca tattgattgg catctcgaaa tgtaagtggc aggctttacc       2460
agctcgtact tgatactaaa cgccgcttag tggtctcgct gtcgttttcg ccgaagacgt       2520
gacatccatt tcggcccccac ctggtatgca tccttcttgc cgcggcccgt gtccctgcta      2580
acttgcattt ctccagccgc gtgggacgac ttgtgcccca tatatgatgc tttgagcgac       2640
aacgacaaag gaggcatcgt tccgtcctga t                                      2671
```

<210> SEQ ID NO 3
<211> LENGTH: 1722
<212> TYPE: DNA
<213> ORGANISM: Artificial Sequence
<220> FEATURE:
<223> OTHER INFORMATION: cDNA

<400> SEQUENCE: 3

```
agatctactt ccagttgctt aacacctcat ccagcgcgta ctgctacacc taccaacgat         60
gtttccaggc gcacggattc ttgctacgct taccttggct cttcatcttt tacatgggac        120
tcatgctgcc atcgggccca ctggcaacat gtacatcgtc aacgaggacg tctctcctga        180
tggtttcgct cgttcggcgg ttgtcgctcg ctcggtgccc gccacagatc cgacgcctgc        240
gacagtatcc attcctggcg ttctcgttca aggaaacaag ggtgataact tccagctgaa        300
cgtcgtcaat caattatcgg acacgaccat gttgaagacg accagtatcc attggcacgg       360
tttcttccaa gccggatctt cgtgggctga tggtcccgct ttcgtgaccc aatgccccgt        420
cgcctctggg gatagtttcc tgtacaattt caatgtacca gaccaagctg gaacattttg        480
gtatcactcg catctttcca cccaatattg tgacggcctc agaggaccat ttgtggtata        540
cgacccctcg gatccgcact tgagtttata cgatattgac aacgctgaca cggtcattac        600
gcttgaggat tggtatcata tcgtggcccc tcaaaacgcg gcgatcccca ccccggatag        660
tactctcatc aatggtaaag gtcgttacgc cgggggccct acctcccctt tgtccatcat        720
caacgtcgaa agcaacaagc gctatcgttt cagacttgtc tcattgtctt gcgatcctaa        780
tttcacgttc tcgatcgacg gtcactcttt gctcgtcatt gaagcagatg ctgtcaacat        840
```

```
tgtacccatc accgtggata gtattcagat cttcgctggc aacgctact ccttcgtctt     900
gactgctgat cagaccattg gcaattactg gattcgcgcg aatcctaact tgggatcgac    960
tggtttcgac ggtggtatca attccgctat tcttcgatat gctggtgcca ctgaggatga   1020
ccctactaca acttcgtcga cgagcacccc attgctggag accaaccttg ttccgcttga   1080
gaatcctggc gctcctggcc cagccgtgcc tggtggagca gacatcaaca tcaatctcgc   1140
tatggccttc gacttcacta acttcgaatt gactatcaac ggcgttcctt tcattccacc   1200
gactgcccct gtccttctcc aaattctctc aggagcctcg actgctgcat cgcttcttcc   1260
ttccggtagc atttacgagc tggaagctaa caaagttgtc gaaatctcga tacctgcgct   1320
ggctgttggg ggaccccatc cgttccatct tcacggtcac accttcgacg ttattaggag   1380
tgcgggttcc actacgtaca acttcgacac tcctgcgcgc cgcgacgttg tcaacactgg   1440
cactgatgcg aacgacaacg tcactattcg cttcgtgacc gacaacccag gcccgtggtt   1500
cctccactgt catattgatt ggcatctcga aattggtctc gctgtcgttt cgccgaaga   1560
cgtgacatcc atttcggccc cacctgccgc gtgggacgac ttgtgcccca tatatgatgc   1620
tttgagcgac aacgacaaag gaggcatcgt tccgtcctaa gagcagcttc tatttattcc   1680
taatttctac ttcttgaatc aattggaaat cacgtcgaaa gg                      1722
```

<210> SEQ ID NO 4
<211> LENGTH: 533
<212> TYPE: PRT
<213> ORGANISM: Pleurotus ostreatus
<220> FEATURE:
<221> NAME/KEY: VARIANT
<222> LOCATION: (1)...(533)
<223> OTHER INFORMATION: amino acid sequence encoded by SEQ ID NO. 3

<400> SEQUENCE: 4

Met Phe Pro Gly Ala Arg Ile Leu Ala Thr Leu Thr Leu Ala Leu His
 1               5                  10                  15

Leu Leu His Gly Thr His Ala Ala Ile Gly Pro Thr Gly Asn Met Tyr
                20                  25                  30

Ile Val Asn Glu Asp Val Ser Pro Asp Gly Phe Ala Arg Ser Ala Val
            35                  40                  45

Val Ala Arg Ser Val Pro Ala Thr Asp Pro Thr Pro Ala Thr Val Ser
        50                  55                  60

Ile Pro Gly Val Leu Val Gln Gly Asn Lys Gly Asp Asn Phe Gln Leu
65                  70                  75                  80

Asn Val Val Asn Gln Leu Ser Asp Thr Thr Met Leu Lys Thr Thr Ser
                85                  90                  95

Ile His Trp His Gly Phe Phe Gln Ala Gly Ser Ser Trp Ala Asp Gly
            100                 105                 110

Pro Ala Phe Val Thr Gln Cys Pro Val Ala Ser Gly Asp Ser Phe Leu
        115                 120                 125

Tyr Asn Phe Asn Val Pro Asp Gln Ala Gly Thr Phe Trp Tyr His Ser
    130                 135                 140

His Leu Ser Thr Gln Tyr Cys Asp Gly Leu Arg Gly Pro Phe Val Val
145                 150                 155                 160

Tyr Asp Pro Ser Asp Pro His Leu Ser Leu Tyr Asp Ile Asp Asn Ala
                165                 170                 175

Asp Thr Val Ile Thr Leu Glu Asp Trp Tyr His Ile Val Ala Pro Gln
            180                 185                 190

```
Asn Ala Ala Ile Pro Thr Pro Asp Ser Thr Leu Ile Asn Gly Lys Gly
            195                 200                 205

Arg Tyr Ala Gly Gly Pro Thr Ser Pro Leu Ser Ile Ile Asn Val Glu
    210                 215                 220

Ser Asn Lys Arg Tyr Arg Phe Arg Leu Val Ser Leu Ser Cys Asp Pro
225                 230                 235                 240

Asn Phe Thr Phe Ser Ile Asp Gly His Ser Leu Leu Val Ile Glu Ala
                245                 250                 255

Asp Ala Val Asn Ile Val Pro Ile Thr Val Asp Ser Ile Gln Ile Phe
                260                 265                 270

Ala Gly Gln Arg Tyr Ser Phe Val Leu Thr Ala Asp Gln Thr Val Gly
            275                 280                 285

Asn Tyr Trp Ile Arg Ala Asn Pro Asn Leu Gly Ser Thr Gly Phe Asp
    290                 295                 300

Gly Gly Ile Asn Ser Ala Ile Leu Arg Tyr Ala Gly Ala Thr Glu Asp
305                 310                 315                 320

Asp Pro Thr Thr Thr Ser Ser Thr Ser Thr Pro Leu Leu Glu Thr Asn
                325                 330                 335

Leu Val Pro Leu Glu Asn Pro Gly Ala Pro Gly Pro Ala Val Pro Gly
            340                 345                 350

Gly Ala Asp Ile Asn Ile Asn Leu Ala Met Ala Phe Asp Phe Thr Asn
355                 360                 365

Phe Glu Leu Thr Ile Asn Gly Val Pro Phe Ile Pro Pro Thr Ala Pro
    370                 375                 380

Val Leu Leu Gln Ile Leu Ser Gly Ala Ser Thr Ala Ala Ser Leu Leu
385                 390                 395                 400

Pro Ser Gly Ser Ile Tyr Glu Leu Glu Ala Asn Lys Val Val Glu Ile
                405                 410                 415

Ser Ile Pro Ala Leu Ala Val Gly Gly Pro His Pro Phe His Leu His
            420                 425                 430

Gly His Thr Phe Asp Val Ile Arg Ser Ala Gly Ser Thr Thr Tyr Asn
    435                 440                 445

Phe Asp Thr Pro Ala Arg Arg Asp Val Val Asn Thr Gly Thr Asp Ala
    450                 455                 460

Asn Asp Asn Val Thr Ile Arg Phe Val Thr Asp Asn Pro Gly Pro Trp
465                 470                 475                 480

Phe Leu His Cys His Ile Asp Trp His Leu Glu Ile Gly Leu Ala Val
                485                 490                 495

Val Phe Ala Glu Asp Val Thr Ser Ile Ser Ala Pro Pro Ala Ala Trp
                500                 505                 510

Asp Asp Leu Cys Pro Ile Tyr Asp Ala Leu Ser Asp Asn Asp Lys Gly
            515                 520                 525

Gly Ile Val Pro Ser
        530
```

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
agatctactt ccagttgctt aacacc                                    26

-continued

```
<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tctagaggat caggacggaa cgatgcctcc                                    30

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
agatctactt ccagttgctt aacacc                                        26

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
cctttcgacg tgatttcc                                                 18
```